US011433081B2

United States Patent
Bonner

(10) Patent No.: US 11,433,081 B2
(45) Date of Patent: Sep. 6, 2022

(54) COMPOSITIONS AND METHODS FOR PAIN MANAGEMENT

(71) Applicant: LoMed, Inc., Levittown, PA (US)

(72) Inventor: Dennis J. Bonner, New Hope, PA (US)

(73) Assignee: LoMed, Inc., Levittown, PA (US)

( * ) Notice: Subject to any disclaimer, the term of this patent is extended or adjusted under 35 U.S.C. 154(b) by 238 days.

(21) Appl. No.: 16/960,286

(22) PCT Filed: Jan. 7, 2019

(86) PCT No.: PCT/US2019/012493
§ 371 (c)(1),
(2) Date: Jul. 6, 2020

(87) PCT Pub. No.: WO2019/136355
PCT Pub. Date: Jul. 11, 2019

(65) Prior Publication Data
US 2021/0052602 A1 Feb. 25, 2021

Related U.S. Application Data

(60) Provisional application No. 62/743,189, filed on Oct. 9, 2018, provisional application No. 62/709,044, filed on Jan. 5, 2018.

(51) Int. Cl.

| | | |
|---|---|---|
| *A61K 31/5513* | (2006.01) |
| *A61P 23/00* | (2006.01) |
| *A61K 31/166* | (2006.01) |
| *A61K 31/195* | (2006.01) |
| *A61K 31/225* | (2006.01) |
| *A61K 31/365* | (2006.01) |
| *A61K 31/4178* | (2006.01) |
| *A61K 31/439* | (2006.01) |
| *A61K 31/4468* | (2006.01) |
| *A61K 31/485* | (2006.01) |
| *A61K 31/495* | (2006.01) |
| *A61K 31/55* | (2006.01) |
| *A61K 47/38* | (2006.01) |

(52) U.S. Cl.
CPC ........ *A61K 31/5513* (2013.01); *A61K 31/166* (2013.01); *A61K 31/195* (2013.01); *A61K 31/225* (2013.01); *A61K 31/365* (2013.01); *A61K 31/4178* (2013.01); *A61K 31/439* (2013.01); *A61K 31/4468* (2013.01); *A61K 31/485* (2013.01); *A61K 31/495* (2013.01); *A61K 31/55* (2013.01); *A61K 47/38* (2013.01); *A61P 23/00* (2018.01)

(58) Field of Classification Search
CPC ... A61K 31/439; A61K 31/495; A61K 31/195
See application file for complete search history.

(56) References Cited

PUBLICATIONS

Popa et al. Journal of Physiology and Pharmacology, 2016, vol. 67, No. 3, pp. 465-469 (Year: 2016).*
Fassoulaki et al. European Journal of Anaesthesiology, 2007, vol. 24, pp. 521-528 (Year: 2007).*
Beaver et al. Advances in Pain Research and Therapy, vol. 1, edited by J.J. Bonica and D. Albe-Fessard, Raven Press, New York, 1976, pp. 553-557 (Year: 1976).*
Hupert et al. Anesth. Analg., 1980, vol. 59, pp. 690-696 (Year: 1980).*
Rumore et al. Pain, 1986, vol. 25, pp. 7-22 (Year: 1986).*
Glazier et al. DICP, 1990, vol. 24, No. 11, pp. 1123-1124 (Abstract attached) (Year: 1990).*
Stambaugh et al. Cancer Invest., 1984, vol. 1, No. 2, pp. 111-117 (Abstract attached) (Year: 1984).*
Peng et al. Medicine, 2017, 96:15, e6463, 11 pages (Year: 2017).*

* cited by examiner

*Primary Examiner* — James D. Anderson
(74) *Attorney, Agent, or Firm* — Goodwin Procter LLP

(57) ABSTRACT

Disclosed herein, in part, are pharmaceutical compositions comprising an opioid agonist such as codeine or a pharmaceutically acceptable salt thereof, hydroxyzine or a pharmaceutically acceptable salt thereof, a gabapentinoid, optionally a 5-HT3 antagonist and a pharmaceutically acceptable excipient. Methods of treating neuropathic and nociceptive pain comprising administering a disclosed pharmaceutical composition to a subject in need thereof is also provided herein

22 Claims, No Drawings

COMPOSITIONS AND METHODS FOR PAIN MANAGEMENT

CROSS-REFERENCE

This application is a national stage entry under 35 U.S.C. § 371 (b) of International Application No. PCT/US2019/012493, filed Jan. 7, 2019, which claims the benefit of, and priority to, U.S. Provisional Application No. 62/709,044 filed Jan. 5, 2018; and U.S. Provisional Application No. 62/743,189, filed Oct. 9, 2018, the contents of each of which are hereby incorporated by reference in their entirety.

BACKGROUND

Opioids, also known as opioid agonists, are a group of drugs that exhibit opium or morphine-like properties. Opioids are used primarily as moderate to strong analgesics. Opioids act as agonists, interacting with stereospecific and saturable binding sites in the brain and other tissues. Endogenous opioid-like peptides are present in areas of the central nervous system that are presumed to be related to the perception of pain. The pharmacologically active principles of opioids reside in their alkaloids, which include morphine, codeine, and papaverine.

The potential for the development of tolerance and physical dependence with repeated opioid usage is an alarming characteristic feature of opioid drugs. The possibility of developing a psychological dependence is also one of the major concerns in the use of opioids to treat pain.

The United States is suffering from a so-called "opioid epidemic". It has been proposed that the onset of this epidemic occurs in physician offices. In November 2016, the Centers for Disease Control (CDC) published guidelines for the treatment of non-cancer related pain. In these guidelines, the CDC suggested limitations as to the amount of morphine milligram equivalencies (MME) that are allowed for adequate pain relief, while limiting the complication rate. Even though there is a legitimate clinical need, the CDC limits have resulted in many physicians being reluctant to prescribe opioids and patients are left to suffer from pain.

These guidelines published by the CDC indicate that the MME should be below 90. Many patients are on high dose OxyContin (e.g., 80 mg/TID) which e.g., provides a MME of 360.

The need for pain relief, e.g., for patients suffering from chronic pain, for example, both nociceptic and neuropathic pain continues to be high. However, there is also a serious need for such pain relief to comply with the MME threshold value.

It is clear that there is an ongoing need for novel compositions that are safer and more effective for pain relief but still comply with, for example, CDC statutes.

SUMMARY

Provided herein are compositions that, while e.g., providing below or about 90 MME of an opioid, can provide significant (e.g., similar) pain relief to a patient as compared to administration of compositions having significantly higher MME of an opioid. For example, provided herein is a pharmaceutical composition comprising codeine or a pharmaceutically acceptable salt thereof; hydroxyzine or a pharmaceutically acceptable salt thereof; a gabapentinoid; optionally a 5-HT3 antagonist; and a pharmaceutically acceptable excipient. For example, provided herein is a pharmaceutical composition for treating neuropathic and deep tissue pain, comprising: about 60 mg or about 120 mg codeine phosphate; about 50 mg or about 100 mg hydroxyzine HCl; about 4 mg ondansetron HCl; about 300 mg or about 1200 mg gabapentin; about 100 mg docusate sodium; and a pharmaceutically acceptable excipient for controlled release.

An exemplary contemplated pharmaceutical composition may include about 60 mg or 120 mg codeine phosphate; about 20 mg to about 100 mg hydroxyzine HCl; optionally about 150 mg to about 600 mg gabapentin; and a pharmaceutically acceptable excipient. For example, provided herein is a unit pharmaceutical composition comprising: about 30 mg or about 60 mg codeine phosphate; about 25 mg or about 50 mg hydroxyzine HCl; about 150 mg, about 300 mg, about 600 mg, or about 1200 mg gabapentin; about 2 mg ondansetron HCl; about 50 mg docusate sodium; and a pharmaceutically acceptable excipient.

A contemplated pharmaceutical composition may also include an opioid agonist or a pharmaceutically acceptable salt thereof; hydroxyzine or a pharmaceutically acceptable salt thereof; a gabapentinoid, such as disclosed herein; optionally a 5-HT3 antagonist such as disclosed herein; and a pharmaceutically acceptable excipient.

A contemplated method of treating neuropathic and nociceptive pain in a patient in need thereof comprises administering to the patient any of the compositions disclosed herein.

In another aspect, provided herein is a kit for pain management comprising: a unit pharmaceutical composition comprising about 60 mg or 120 mg codeine phosphate; about 25 mg, about 50 mg or about 100 mg hydroxyzine HCl and a pharmaceutically acceptable excipient; about 150 mg, 300 mg, about 600 mg, or about 1200 mg gabapentin; about 2 mg or about 4 mg ondansetron HCl; and optionally about 50 mg or about 100 mg docusate sodium.

DETAILED DESCRIPTION

The present disclosure provides, in part, pharmaceutical compositions that include an opioid agonist (such as codeine) or a pharmaceutically acceptable salt thereof, and hydroxyzine or a pharmaceutically acceptable salt thereof, and may also include a gabapentinoid, optionally a 5-HT3 antagonist (e.g., ondansetron), optionally a stool softener (e.g., docusate sulfate) and a pharmaceutically acceptable excipient. Methods of treating neuropathic and/or nociceptive pain comprising administering a disclosed pharmaceutical composition to a subject in need thereof are also provided herein.

Definitions

Unless defined otherwise, all technical and scientific terms used herein have the same meaning as is commonly understood by one of skill in the art to which this specification pertains.

As used herein, the singular form "a", "an" and "the" includes plural references unless the context clearly dictates otherwise.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

"Subject" "individual", and "patient" are used interchangeably and refer to which administration is contemplated includes, but is not limited to, humans (e.g., a male or female of any age group, e.g., a pediatric subject (e.g., infant, child, adolescent) or adult subject (e.g., young adult, middle-aged adult or senior adult)).

"A patient in need," as used herein, refers to a patient suffering from any of the symptoms or manifestations of a neuropathic and/or nociceptive pain, a patient who may suffer from any of the symptoms or manifestations of neuropathic and/or nociceptive pain, or any patient who might benefit from a method of the disclosure for treating a neuropathic and/or nociceptive pain.

The terms "treat", "treatment", "treating" and the like are used herein to generally mean obtaining a desired pharmacological and/or physiological effect. The effect may be prophylactic in terms of completely or partially preventing a neuropathic and/or nociceptive pain or symptom thereof and/or may be therapeutic in terms of partially or completely curing a neuropathic and/or nociceptive pain and/or adverse effect attributed to a neuropathic and/or nociceptive pain.

"Pharmaceutically acceptable" includes molecular entities and compositions that do not produce an adverse, allergic or other untoward reaction when administered to an animal, or a human, as appropriate.

"Pharmaceutically acceptable salt" as used herein, refers to any salt of a compound of the disclosure which retains its biological properties and which is not toxic or otherwise undesirable for pharmaceutical use. Pharmaceutically acceptable salts may be derived from a variety of organic and inorganic counter-ions well known in the art. For example, Berge et al. describes pharmaceutically acceptable salts in detail in J. Pharmaceutical Sciences (1977) 66: 1-19. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

"Codeine" as used herein refers to codeine in the form of a free acid or its pharmaceutically acceptable salts. Codeine is a mild analgesic used in the relief of mild to moderately severe pain that is not relieved by a non-opiate analgesic.

Hydroxyzine is a histamine H1 receptor antagonist. Hydroxyzine or a pharmaceutically acceptable salt thereof blocks the H1 histamine receptor and prevents the symptoms that are caused by histamine activity on capillaries, bronchial smooth muscle, and gastrointestinal smooth muscle, including vasodilation, increased capillary permeability, bronchoconstriction, and spasmodic contraction of gastrointestinal smooth muscle. In addition, hydroxyzine crosses the blood-brain barrier and acts on the histamine H1-receptors in the central nervous systems.

Gabapentinoids are a class of drugs that are derivatives of the inhibitory neurotransmitter γ-aminobutyric acid (GABA) which selectively block $Ca^{2+}$ channels containing the $\alpha_2\delta$-1 subunit. Exemplary gabapentinoids for use in a disclosed composition can include, but are not limited to, gabapentin, gabapentin enacarbil, atagabalin, pregabalin, phenibut, microgablin, 4-methylpregabalin, and PD-217,014. In some embodiments, the gabapentinoid is gabapentin or a pharmaceutically acceptable salt thereof. Gabapentin is an anticonvulsant that is widely used as adjunctive therapy in the management of neuropathic pain syndromes. The physiologic effect of gabapentin is by means of decreased central nervous system disorganized electrical activity.

5-HT3 antagonists are a class of drugs that act as receptor antagonists at the $5-HT_3$ receptor, a subtype of serotonin receptor found in terminals of the vagus nerve and in certain areas of the brain. Most $5-HT_3$ antagonists are antiemetics, which are used in the prevention and treatment of nausea and vomiting caused by certain medications and have reported anxiolytic and neuroleptic properties. Exemplary 5-HT3 antagonists include, but are not limited to, a setron agent, galanolactone, mirtazapine, olanzapine, cisapride, renzapride and metoclopramide. Exemplary setron agents include, but are not limited to, ondansetron, tropisetron, granisetron, dolasetron, palonosetron and ramosetron.

Throughout the description, where compositions and kits are described as having, including, or comprising specific components, or where processes and methods are described as having, including, or comprising specific steps, it is contemplated that, additionally, there are compositions and kits of the present disclosure that consist essentially of, or consist of, the recited components, and that there are processes and methods according to the present disclosure that consist essentially of, or consist of, the recited processing steps.

As a general matter, compositions specifying a percentage are by weight unless otherwise specified. Further, if a variable is not accompanied by a definition, then the previous definition of the variable controls.

Pharmaceutical Compositions

The present disclosure is directed in part to a pharmaceutical composition comprising an opioid agonist or pharmaceutically acceptable salt thereof (e.g., codeine or a pharmaceutically acceptable salt thereof, for example codeine phosphate or codeine sulfate) and hydroxyzine or a pharmaceutically acceptable salt thereof (e.g., hydroxyzine pamoate or hydroxyzine HCl), and optionally a gabapentinoid, optionally a 5-HT3 antagonist, and a pharmaceutically acceptable excipient, wherein for example, a dose of a disclosed composition provides less than about 18 MME, or about 20 MME, of opioid to the patient, and/or the daily doses provide less than or about 50 MME or 54 MME, or below or about 90 MME.

For example, a provided pharmaceutical composition, when administered to a patient one, two or three times daily, even while e.g., providing below or about 90 MME of opioid, provides a substantially lower pain score, substantially less dysphoria and/or withdrawal symptoms, and/or increased mental clarity as compared to a patient's pain score when administered a fentanyl patch 50 μg or 70 μg; oxycodone 15 mg orally every 6 hours, 2 times daily or 4 times daily, oxycodone 30 mg twice daily, morphine 30 mg every 12 hours, or any combination thereof, and/or a substantially lower pain score, substantially less dysphoria and/or withdrawal symptoms, and/or increased mental clarity as compared to when administered e.g., a MME of 120 or higher of an opioid alone.

In an aspect, a pharmaceutical composition comprising an opioid agonist or pharmaceutically acceptable salt thereof, hydroxyzine or a pharmaceutically acceptable salt thereof, a gabapentinoid, optionally a 5-HT3 antagonist, and a pharmaceutically acceptable excipient is provided. In some embodiments, a contemplated pharmaceutical composition may be a unit pharmaceutical composition. For example, a contemplated pharmaceutical composition may include gabapentin and ondansetron HCl. In some embodiments, a contemplated composition may include a pharmaceutically acceptable excipient such as methyl cellulose, e.g., Methocel™ KM100CR.

Contemplated compositions may include one or more opioid agonists. Such opioid agonists may include, but are not limited to, one or more of: hydrocodone, oxycodone, acetyldihydrocodeinone, diamorphine, codeine, pethidine, alfentanil, buprenorphine, butorphanol, codeine, dezocine, fentanyl, hydromorphone, levomethadyl acetate, levorphanol, meperidine, methadone, morphine sulfate, nalbuphine, oxymorphone, pentazocine, propoxyphene, remifentanil, sufentanil, tramadol, or pharmaceutically acceptable salts thereof, e.g., together with hydroxyzine and/or dextromethorphan, and for example, a dose of such a composition may provide less than about 18, or about 20 MME, of opioid to the patient, and/or daily doses provide less than or about 50 or 54 MME, or below or about 90 MME.

In some embodiments, a disclosed pharmaceutical composition comprises an opioid agonist or a pharmaceutically acceptable salt thereof in an amount in the range of about 20 mg, about 30 mg, about 40 mg, about 50 mg, about 60 mg, about 70 mg, about 80 mg, about 90 mg, about 100 mg, about 110 mg, about 120 mg, about 130 mg, or about 140 mg. In some embodiments, a disclosed pharmaceutical composition comprises an opioid agonist or a pharmaceutically acceptable salt thereof in an amount in the range of from about 20 mg to about 140 mg, from about 40 mg to about 140 mg, from about 60 mg to about 140 mg, from about 80 mg to about 140 mg, from about 100 mg to about 140 mg, from about 120 mg to about 140 mg, from about 20 mg to about 120 mg, from about 20 mg to about 100 mg, from about 20 mg to about 80 mg, from about 20 mg to about 60 mg, from about 20 mg to about 40 mg, from about 40 mg to about 120 mg, from about 40 mg to about 100 mg, from about 40 mg to about 80 mg, from about 40 mg to about 60 mg, from about 60 mg to about 120 mg, from about 60 mg to about 100 mg, from about 60 mg to about 80 mg, from about 80 mg to about 120 mg, from about 80 mg to about 100 mg, or from about 100 mg to about 120 mg. In some embodiments, a disclosed pharmaceutical composition comprises an opioid agonist or a pharmaceutically acceptable salt thereof in an amount in the range of from about 20 mg to about 120 mg. In some embodiments, the opioid agonist is codeine or a pharmaceutically acceptable salt thereof.

In some embodiments, a disclosed pharmaceutical composition comprises hydroxyzine or a pharmaceutically acceptable salt thereof in an amount in the range of from about 10 mg to about 110 mg, from about 20 mg to about 110 mg, from about 30 mg to about 110 mg, from about 40 mg to about 110 mg, from about 50 mg to about 110 mg, from about 60 mg to about 110 mg, from about 70 mg to about 110 mg, from about 80 mg to 110 mg, from about 90 mg to about 110 mg, from about 100 mg to about 110 mg, from about 10 mg to about 100 mg, from about 10 mg to about 90 mg, from about 10 mg to about 80 mg, from about 10 mg to about 70 mg, from about 10 mg to about 60 mg, from about 10 mg to about 50 mg, from about 10 mg to about 40 mg, from about 10 mg to about 30 mg, from about 10 mg to about 20 mg, from about 20 mg to about 100 mg, from about 20 mg to about 90 mg, from about 20 mg to about 80 mg, from about 20 mg to about 70 mg, from about 20 mg to about 60 mg, from about 20 mg to about 50 mg, from about 20 mg to about 40 mg, from about 20 mg to about 30 mg, from about 30 mg to about 100 mg, from about 30 mg to about 90 mg, from about 30 mg to about 80 mg, from about 30 mg to about 70 mg, from about 30 mg to about 60 mg, from about 30 mg to about 50 mg, from about 30 mg to about 40 mg, from about 40 mg to about 100 mg, from about 40 mg to about 90 mg, from about 40 mg to about 80 mg, from about 40 mg to about 70 mg, from about 40 mg to about 60 mg, from about 40 mg to about 50 mg, from about 50 mg to about 100 mg, from about 50 mg to about 90 mg, from about 50 mg to about 80 mg, from about 50 mg to about 70 mg, from about 50 mg to about 60 mg, from about 60 mg to about 100 mg, from about 60 mg to about 90 mg, from about 60 mg to about 80 mg, from about 60 mg to about 70 mg, from about 70 mg to about 100 mg, from about 70 mg to about 90 mg, from about 70 mg to about 80 mg, from about 80 mg to about 100 mg, from about 80 mg to about 90 mg, or from about 90 mg to about 100 mg. In some embodiments, a disclosed pharmaceutical composition comprises hydroxyzine or a pharmaceutically acceptable salt thereof in an amount in the range of from about 10 mg to about 110 mg. In some embodiments, a disclosed pharmaceutical composition comprises hydroxyzine or a pharmaceutically acceptable salt thereof in an amount of about 10 mg, about 15 mg, about 20 mg, about 25 mg, about 30 mg, about 40 mg, about 50 mg, about 60 mg, about 70 mg, about 80 mg, about 90 mg, about 100 mg, or about 110 mg. In some embodiments, the pharmaceutically acceptable salt of hydroxyzine is hydroxyzine HCl or hydroxyzine pamoate. In some embodiments, the pharmaceutically acceptable salt of hydroxyzine is hydroxyzine HCl.

For example, a disclosed pharmaceutical composition may include about 25 mg, about 50 mg, or about 100 mg hydroxyzine HCl and e.g. a codeine salt as disclosed herein.

It should be noted that in some embodiments, dextromethorphan can be used in the contemplated pharmaceutical compositions instead of, or in addition to hydroxyzine or a pharmaceutically acceptable salt thereof.

Contemplated gabapentinoids that may be present in a disclosed pharmaceutical composition may be selected from the group consisting of gabapentin, gabapentin encarbil, and atagabalin. In some embodiments, the gabapentinoid is gabapentin or a pharmaceutically acceptable salt thereof.

5-HT3 antagonists for use in a disclosed composition may be selected from the group consisting of a setron agent, galanolactone, mirtazapine, olanzapine, cisapride, renzapride and metoclopramide. For example, the setron agent may be selected from the group consisting of ondansetron, tropisetron, granisetron, dolasetron, palonosetron and ramosetron. In some embodiments, the setron agent is ondansetron or a pharmaceutically acceptable salt thereof. In some embodiments the pharmaceutically acceptable salt of ondansetron is ondansetron hydrochloride.

In an embodiment, a contemplated pharmaceutical composition further comprises gabapentin and a setron agent in addition to e.g. a codeine salt. In some embodiments, a contemplated pharmaceutical composition further comprises gabapentin and ondansetron HCl.

In some embodiments, the pharmaceutical composition comprises gabapentin or a pharmaceutically acceptable salt thereof in an amount in the range of from about 50 mg to about 1200 mg, from about 100 mg to about 1200 mg, from about 200 mg to about 1200 mg, from about 300 mg to about 1200 mg, from about 400 mg to about 1200 mg, from about 500 mg to about 1200 mg, from about 600 mg to about 1200 mg, from about 700 mg to about 1200 mg, from about 800 mg to about 1200 mg, from about 800 mg to about 1200 mg, from about 800 mg to about 1200 mg, from about 900 mg to about 1200 mg, from about 1000 mg to about 1200 mg, from about 1100 mg to about 1200 mg, from about 100 mg to about 1100 mg, from about 100 mg to about 1000 mg, from about 100 mg to about 900 mg, from about 100 mg to about 800 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg, from about 200 mg to about 1100 mg, from about 200 mg to about 1000 mg, from about 200 mg to about 900 mg, from about 200 mg to about 800 mg, from about 200 mg to about 700 mg, from about 200 mg to about 600 mg, from about 200 mg to about 500 mg, from about 200 mg to about 400 mg, from about 200 mg to about 300 mg, from about 300 mg to about 1100 mg, from about 300 mg to about 1000 mg, from about 300 mg to about 900 mg, from about 300 mg to about 800 mg, from about 300 mg to about 700 mg, from about 300 mg to about 600 mg, from about 300 mg to about 500 mg, from about 300 mg to about 400 mg, from about 400 mg to about 1100 mg, from about 400 mg to about 1000 mg, from about 400 mg to about 900 mg, from about 400 mg to about 800 mg, from about 400 mg to about 700 mg, from about 400 mg to about 600 mg, from about 400 mg to about 500 mg, from about 500 mg to about 1100 mg, from about 500 mg to about 1000 mg, from about 500 mg to about 900 mg, from about 500 mg to about 800 mg, from about 500 mg to about 700 mg, from about 500 mg to about 600 mg, from about 600 mg to about 1100 mg, from about 600 mg to about 1000 mg, from about 600 mg to about 900 mg, from about 600 mg to about 800 mg, from about 600 mg to about 700 mg, from about 700 mg to about 1100 mg, from about 700 mg to about 1000 mg, from about 700 mg to about 900 mg, from about 700 mg to about 800 mg, from about 800 mg to about 1100 mg, from about 800 mg to about 1000 mg, from about 800 mg to about 900 mg, from about 900 mg to about 1100 mg, from about 900 mg to about 1000 mg, or from about 1000 mg to about 1100 mg. In some embodiments, a disclosed pharmaceutical composition may include gabapentin or a pharmaceutically acceptable salt thereof in an amount in the range of from about 100 mg to about 1200 mg. In some embodiments, the pharmaceutical composition comprises gabapentin or a pharmaceutically acceptable salt thereof in an amount of about 100 mg, about 150 mg, about 200 mg, about 300 mg, about 400 mg, about 500 mg, about 600 mg, about 700 mg, about 800 mg, about 900 mg, about 1000 mg, about 1100 mg, or about 1200 mg. In some embodiments, the pharmaceutical composition comprises gabapentin or a pharmaceutically acceptable salt thereof in an amount of about 150 mg, about 300 mg, or about 600 mg.

In some embodiments, a disclosed pharmaceutical composition comprises ondansetron HCl in an amount in the range of from about 1 mg to about 5 mg, from about 2 mg to about 5 mg, from about 3 mg to about 5 mg, from about 4 mg to about 5 mg, from about 1 mg to about 4 mg, from about 1 mg to about 3 mg, from about 1 mg to about 2 mg, from about 2 mg to about 4 mg, from about 2 mg to about 3 mg, or from about 3 mg to about 4 mg. In some embodiments, the pharmaceutical composition comprises ondansetron HCl in an amount of about 1 mg or about 4 mg. In some embodiments, the pharmaceutical composition comprises ondansetron HCl in an amount of about 2 mg or about 4 mg.

A contemplated pharmaceutical composition may, in some embodiments, further comprise a stool softener and/or a constipation agent. In some embodiments, the stool softener or constipation agent is docusate or a pharmaceutically acceptable salt thereof, or naloxegol. In some embodiments, the stool softener is docusate or a pharmaceutically acceptable salt thereof. In some embodiments, the constipation agent is naloxegol. In some embodiments, the pharmaceutically acceptable salt of docusate is docusate sodium.

In some embodiments, the pharmaceutical composition further comprises docusate sodium in an amount of about 25 mg, about 50 mg, about 75 mg, or about 100 mg. In some embodiments, the pharmaceutical composition comprises docusate sodium in an amount of about 50 mg, or about 100 mg.

In some embodiments, a contemplated pharmaceutical composition comprises a pharmaceutically acceptable excipient, such as a methyl cellulose (e.g., Methocel™ KM100CR). In some embodiments, the pharmaceutically acceptable excipient is Methocel™ KM100CR.

In an aspect, a pharmaceutical composition is provided that comprises codeine or a pharmaceutically acceptable salt thereof, hydroxyzine or a pharmaceutically acceptable salt thereof, a gabapentinoid, optionally a 5-HT3 antagonist, and a pharmaceutically acceptable excipient. In some embodiments, such a disclosed pharmaceutical composition is a unit pharmaceutical composition.

In some embodiments, a disclosed pharmaceutical composition comprises codeine or a pharmaceutically acceptable salt thereof in an amount in the range of about 20 mg, about 30 mg, about 40 mg, about 50 mg, about 60 mg, about 70 mg, about 80 mg, about 90 mg, about 100 mg, about 110 mg, about 120 mg, about 130 mg, or about 140 mg. In some embodiments, a disclosed pharmaceutical composition comprises codeine or a pharmaceutically acceptable salt thereof in an amount in the range of from about 20 mg to about 140 mg, from about 40 mg to about 140 mg, from about 60 mg to about 140 mg, from about 80 mg to about 140 mg, from about 100 mg to about 140 mg, from about 120 mg to about 140 mg, from about 20 mg to about 120 mg, from about 20 mg to about 100 mg, from about 20 mg to about 80 mg, from about 20 mg to about 60 mg, from about 20 mg to about 40 mg, from about 40 mg to about 120 mg, from about 40 mg to about 100 mg, from about 40 mg to about 80 mg, from about 40 mg to about 60 mg, from about 60 mg to about 120 mg, from about 60 mg to about 100 mg, from about 60 mg to about 80 mg, from about 80 mg to about 120 mg, from about 80 mg to about 100 mg, or from about 100 mg to about 120 mg. In some embodiments, a disclosed pharmaceutical composition comprises codeine or a pharmaceutically acceptable salt thereof in an amount in the range of from about 20 mg to about 120 mg. In some embodiments, the pharmaceutically acceptable salt of codeine is codeine phosphate or codeine sulfate. In some embodiments, the pharmaceutically acceptable salt of codeine is codeine phosphate.

In some embodiments, a disclosed pharmaceutical composition comprises about 60 mg or about 120 mg codeine phosphate.

In some embodiments, a disclosed pharmaceutical composition comprises hydroxyzine or a pharmaceutically acceptable salt thereof in an amount in the range of from about 10 mg to about 110 mg, from about 20 mg to about 110 mg, from about 30 mg to about 110 mg, from about 40 mg to about 110 mg, from about 50 mg to about 110 mg, from about 60 mg to about 110 mg, from about 70 mg to about 110 mg, from about 80 mg to 110 mg, from about 90 mg to about 110 mg, from about 100 mg to about 110 mg, from about 10 mg to about 100 mg, from about 10 mg to about 90 mg, from about 10 mg to about 80 mg, from about 10 mg to about 70 mg, from about 10 mg to about 60 mg, from about 10 mg to about 50 mg, from about 10 mg to about 40 mg, from about 10 mg to about 30 mg, from about 10 mg to about 20 mg, from about 20 mg to about 100 mg, from about 20 mg to about 90 mg, from about 20 mg to about 80 mg, from about 20 mg to about 70 mg, from about 20 mg to about 60 mg, from about 20 mg to about 50 mg, from about 20 mg to about 40 mg, from about 20 mg to about 30 mg, from about 30 mg to about 100 mg, from about 30 mg to about 90 mg, from about 30 mg to about 80 mg, from about 30 mg to about 70 mg, from about 30 mg to about 60 mg, from about 30 mg to about 50 mg, from about 30 mg to about 40 mg, from about 40 mg to about 100 mg, from about 40 mg to about 90 mg, from about 40 mg to about 80 mg, from about 40 mg to about 70 mg, from about 40 mg to about 60 mg, from about 40 mg to about 50 mg, from about 50 mg to about 100 mg, from about 50 mg to about 90 mg, from about 50 mg to about 80 mg, from about 50 mg to about 70 mg, from about 50 mg to about 60 mg, from about 60 mg to about 100 mg, from about 60 mg to about 90 mg, from about 60 mg to about 80 mg, from about 60 mg to about 70 mg, from about 70 mg to about 100 mg, from about 70 mg to about 90 mg, from about 70 mg to about 80 mg, from about 80 mg to about 100 mg, from about 80 mg to about 90 mg, or from about 90 mg to about 100 mg. In some embodiments, a disclosed pharmaceutical composition comprises hydroxyzine or a pharmaceutically acceptable salt thereof in an amount in the range of from about 10 mg to about 110 mg. In some embodiments, a disclosed pharmaceutical composition comprises hydroxyzine or a pharmaceutically acceptable salt thereof in an amount of about 10 mg, about 15 mg, about 20 mg, about 25 mg, about 30 mg, about 40 mg, about 50 mg, about 60 mg, about 70 mg, about 80 mg, about 90 mg, about 100 mg, or about 110 mg. In some embodiments, the pharmaceutically acceptable salt of hydroxyzine is hydroxyzine HCl or hydroxyzine pamoate. In some embodiments, the pharmaceutically acceptable salt of hydroxyzine is hydroxyzine HCl.

In some embodiments, the pharmaceutical composition comprises about 25 mg, about 50 mg, or about 100 mg hydroxyzine HCl.

It should be noted that in some embodiments, dextromethorphan can be used in the contemplated pharmaceutical compositions instead of, or in addition to hydroxyzine or a pharmaceutically acceptable salt thereof.

Contemplated gabapentinoids that may be present in a disclosed pharmaceutical composition may be selected from the group consisting of gabapentin, gabapentin encarbil, and atagabalin. In some embodiments, the gabapentinoid is gabapentin or a pharmaceutically acceptable salt thereof.

5-HT3 antagonists for use in a disclosed composition may be selected from the group consisting of a setron agent, galanolactone, mirtazapine, olanzapine, cisapride, renzapride and metoclopramide. For example, the setron agent may be selected from the group consisting of ondansetron, tropisetron, granisetron, dolasetron, palonosetron and ramosetron. In some embodiments, the setron agent is ondansetron or a pharmaceutically acceptable salt thereof. In some embodiments the pharmaceutically acceptable salt of ondansetron is ondansetron hydrochloride.

In an embodiment, a contemplated pharmaceutical composition further comprises gabapentin and a setron agent. In some embodiments, a contemplated pharmaceutical composition further comprises gabapentin and ondansetron HCl.

In some embodiments, the pharmaceutical composition comprises gabapentin or a pharmaceutically acceptable salt thereof in an amount in the range of from about 50 mg to about 1200 mg, from about 100 mg to about 1200 mg, from about 200 mg to about 1200 mg, from about 300 mg to about 1200 mg, from about 400 mg to about 1200 mg, from about 500 mg to about 1200 mg, from about 600 mg to about 1200 mg, from about 700 mg to about 1200 mg, from about 800 mg to about 1200 mg, from about 800 mg to about 1200 mg, from about 800 mg to about 1200 mg, from about 900 mg to about 1200 mg, from about 1000 mg to about 1200 mg, from about 1100 mg to about 1200 mg, from about 100 mg to about 1100 mg, from about 100 mg to about 1000 mg, from about 100 mg to about 900 mg, from about 100 mg to about 800 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg, from about 200 mg to about 1100 mg, from about 200 mg to about 1000 mg, from about 200 mg to about 900 mg, from about 200 mg to about 800 mg, from about 200 mg to about 700 mg, from about 200 mg to about 600 mg, from about 200 mg to about 500 mg, from about 200 mg to about 400 mg, from about 200 mg to about 300 mg, from about 300 mg to about 1100 mg, from about 300 mg to about 1000 mg, from about 300 mg to about 900 mg, from about 300 mg to about 800 mg, from about 300 mg to about 700 mg, from about 300 mg to about 600 mg, from about 300 mg to about 500 mg, from about 300 mg to about 400 mg, from about 400 mg to about 1100 mg, from about 400 mg to about 1000 mg, from about 400 mg to about 900 mg, from about 400 mg to about 800 mg, from about 400 mg to about 700 mg, from about 400 mg to about 600 mg, from about 400 mg to about 500 mg, from about 500 mg to about 1100 mg, from about 500 mg to about 1000 mg, from about 500 mg to about 900 mg, from about 500 mg to about 800 mg, from about 500 mg to about 700 mg, from about 500 mg to about 600 mg, from about 600 mg to about 1100 mg, from about 600 mg to about 1000 mg, from about 600 mg to about 900 mg, from about 600 mg to about 800 mg, from about 600 mg to about 700 mg, from about 700 mg to about 1100 mg, from about 700 mg to about 1000 mg, from about 700 mg to about 900 mg, from about 700 mg to about 800 mg, from about 800 mg to about 1100 mg, from about 800 mg to about 1000 mg, from about 800 mg to about 900 mg, from about 900 mg to about 1100 mg, from about 900 mg to about 1000 mg, or from about 1000 mg to about 1100 mg. In some embodiments, the pharmaceutical composition comprises gabapentin or a pharmaceutically acceptable salt thereof in an amount in the range of from about 100 mg to about 1200 mg. In some embodiments, the pharmaceutical composition comprises gabapentin or a pharmaceutically acceptable salt thereof in an amount of about 100 mg, about 150 mg, about 200 mg, about 300 mg, about 400 mg, about 500 mg, about 600 mg, about 700 mg, about 800 mg, about 900 mg, about 1000 mg, about 1100 mg, or about 1200 mg. In some embodiments, the pharmaceutical composition comprises gabapentin or a pharmaceutically acceptable salt thereof in an amount of about 150 mg, about 300 mg, or about 600 mg.

In some embodiments, the pharmaceutical composition comprises ondansetron HCl in an amount in the range of from about 1 mg to about 5 mg, from about 2 mg to about 5 mg, from about 3 mg to about 5 mg, from about 4 mg to about 5 mg, from about 1 mg to about 4 mg, from about 1 mg to about 3 mg, from about 1 mg to about 2 mg, from about 2 mg to about 4 mg, from about 2 mg to about 3 mg, or from about 3 mg to about 4 mg. In some embodiments, the pharmaceutical composition comprises ondansetron HCl in an amount of about 1 mg or about 4 mg. In some embodiments, the pharmaceutical composition comprises ondansetron HCl in an amount of about 2 mg or about 4 mg.

A contemplated pharmaceutical composition may, in some embodiments, further comprise a stool softener and/or a constipation agent. In some embodiments, the stool softener or constipation agent is docusate or a pharmaceutically acceptable salt thereof, or naloxegol. In some embodiments, the stool softener is docusate or a pharmaceutically acceptable salt thereof. In some embodiments, the constipation agent is naloxegol. In some embodiments, the pharmaceutically acceptable salt of docusate is docusate sodium.

In some embodiments, the pharmaceutical composition further comprises docusate sodium in an amount of about 25 mg, about 50 mg, about 75 mg, or about 100 mg. In some embodiments, the pharmaceutical composition comprises docusate sodium in an amount of about 50 mg, or about 100 mg.

In some embodiments, a contemplated pharmaceutical composition comprises a pharmaceutically acceptable excipient, such as a methyl cellulose (e.g., Methocel™ KM100CR). In some embodiments, the pharmaceutically acceptable excipient is Methocel™ KM100CR.

In an aspect, a pharmaceutical composition for treating neuropathic and deep tissue pain comprising about 60 mg or about 120 mg codeine sulfate, about 50 mg or about 100 mg hydroxyzine HCl, about 4 mg ondansetron HCl, about 300 mg or about 600 mg gabapentin, about 100 mg docusate sodium, and a pharmaceutically acceptable excipient for controlled release. In some embodiments, the pharmaceutical composition is a unit pharmaceutical composition.

In an aspect, a pharmaceutical composition comprising about 60 mg or about 120 mg codeine phosphate, about 20 mg to about 100 mg hydroxyzine HCl, optionally about 150 mg to about 1200 mg gabapentin, and a pharmaceutically acceptable excipient. In some embodiments, the pharmaceutical composition is a unit pharmaceutical composition. In a further embodiment, the pharmaceutical composition comprises ondansetron HCl in an amount in the range of from about 1 mg to about 4 mg.

In some embodiments, a contemplated pharmaceutical composition comprises a pharmaceutically acceptable excipient, such as a methyl cellulose (e.g., Methocel™ KM100CR). In some embodiments, the pharmaceutically acceptable excipient is Methocel™ KM100CR.

In an aspect, a unit pharmaceutical composition comprising about 30 mg or about 60 mg codeine phosphate, about 25 mg or about 50 mg hydroxyzine HCl, about 150 mg, about 300 mg, about 600 mg, or about 1200 mg gabapentin, about 2 mg ondansetron HCl, about 50 mg docusate sodium, and a pharmaceutically acceptable excipient. In some embodiments, the codeine phosphate in the unit pharmaceutical composition may be substituted with codeine sulfate.

In some embodiments, a contemplated pharmaceutical composition comprises a pharmaceutically acceptable excipient, such as a methyl cellulose (e.g., Methocel™ KM100CR). In some embodiments, the pharmaceutically acceptable excipient is Methocel™ KM100CR.

In an aspect, the disclosure provides a method of treating neuropathic and/or nociceptive pain in a patient in need thereof, the method comprising administering to the patient a pharmaceutical composition of the present disclosure.

In some embodiments, the method further comprises administering to the patient a second pharmaceutical composition, wherein the second pharmaceutical composition comprises a 5-HT3 antagonist and a stool softener and/or a constipation agent.

5-HT3 antagonists for use in a disclosed composition may be selected from the group consisting of a setron agent, galanolactone, mirtazapine, olanzapine, cisapride, renzapride and metoclopramide. For example, the setron agent may be selected from the group consisting of ondansetron, tropisetron, granisetron, dolasetron, palonosetron and ramosetron. In some embodiments, the setron agent is ondansetron or a pharmaceutically acceptable salt thereof. In some embodiments the pharmaceutically acceptable salt of ondansetron is ondansetron HCl.

In some embodiments, the second pharmaceutical composition comprises ondansetron HCl in an amount in the range of from about 1 mg to about 5 mg, from about 2 mg to about 5 mg, from about 3 mg to about 5 mg, from about 4 mg to about 5 mg, from about 1 mg to about 4 mg, from about 1 mg to about 3 mg, from about 1 mg to about 2 mg, from about 2 mg to about 4 mg, from about 2 mg to about 3 mg, or from about 3 mg to about 4 mg. In some embodiments, the second pharmaceutical composition comprises ondansetron HCl in an amount of about 1 mg or about 4 mg. In some embodiments, the second pharmaceutical composition comprises ondansetron HCl in an amount of about 2 mg or about 4 mg. In some embodiments, the second pharmaceutical composition comprises ondansetron HCl in an amount of about 1 mg, about 2 mg, about 3 mg, about 4 mg, or about 5 mg. In some embodiments, the second pharmaceutical composition comprises ondansetron HCl in an amount of about 4 mg.

In some embodiments, the stool softener or constipation agent is docusate or a pharmaceutically acceptable salt thereof, or naloxegol. In some embodiments, the stool softener is docusate or a pharmaceutically acceptable salt thereof. In some embodiments, the constipation agent is naloxegol. In some embodiments, the pharmaceutically acceptable salt of docusate is docusate sodium.

In some embodiments, the second pharmaceutical composition further comprises docusate sodium in an amount of about 25 mg, about 50 mg, about 75 mg, or about 100 mg. In some embodiments, the second pharmaceutical composition comprises docusate sodium in an amount of about 50 mg, or about 100 mg.

In an aspect, the disclosure provides a method of treating neuropathic and/or nociceptive pain in a patient in need thereof, the method comprising administering to the patient one or more units of a unit pharmaceutical composition of the present disclosure one, two, three, four, five or six times daily.

In an aspect, the disclosure provides a method of treating neuropathic and/or nociceptive pain in a patient in need thereof, the method comprising administering to the patient two units of a unit pharmaceutical composition of the present disclosure three times daily.

Pain intensity in a patient may be assessed, for example, using measures such as the Visual Analogue Scale (VAS), Numerical Rating Scale (NRS), Verbal Rating Scale (VRS), and Faces Pain Scale-Revised (FPS-R).

In some embodiments, the pharmaceutical compositions as disclosed herein, when administered to a patient one, two, or three times daily, provides a substantially lower pain score as compared to a patient's pain score when administered a fentanyl patch 50 µg or 70 µg; oxycodone 15 mg orally every 6 hours, 2 times daily or 4 times daily; oxycodone 30 mg twice daily (or 80 mg TID); morphine 30 mg every 12 hours, or any combination thereof.

In some embodiments, the pharmaceutical compositions as disclosed herein, when administered to a patient one, two, or three times daily, provides substantially less dysphoria or withdrawal symptoms as compared to a patient's pain score when administered a fentanyl patch 50 µg or 70 µg; oxycodone 15 mg orally every 6 hours, 2 times daily or 4 times daily; oxycodone 30 mg twice daily (or 80 mg TID); morphine 30 mg every 12 hours, or any combination thereof.

Formulations

In certain embodiments, the pharmaceutical compositions as described herein are formulated for oral administration.

For example, provided herein are pharmaceutical compositions (e.g., a capsule or tablet) for oral administration comprising e.g., an opioid agonist (e.g., codeine phosphate) and one or more other active ingredients as disclosed herein, and a pharmaceutical excipient suitable for oral administration, e.g., provided herein are pharmaceutical compositions for oral administration containing: (i) codeine or a pharmaceutically acceptable salt thereof; (ii) hydroxyzine or a pharmaceutically acceptable salt thereof; optionally (iii) a gabapentinoid; optionally (iv) a 5-HT3 antagonist; and (v) one or more pharmaceutical excipients suitable for oral administration.

Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by e.g., a step of bringing the active ingredient into association with the carrier or excipient, which constitutes one or more ingredients. In general, a pharmaceutical composition may be prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

An active ingredient can be combined in an intimate admixture with a pharmaceutical carrier according to conventional pharmaceutical compounding techniques. The carrier can take a wide variety of forms depending on the form of preparation desired for administration. In preparing the, pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or non-aqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose (e.g., Methocel™ KM100CR), pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. Disintegrants that can he used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof.

When aqueous suspensions and/or elixirs are desired for oral administration, the active ingredient therein can he combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HUB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopherol PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oilsoluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

The pharmaceutical compositions as disclosed herein may further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives may include, but are not limited to, antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 1 15, Germaben II, Neolone, Kathon, and Euxyl.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savory, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include, but are not limited to, amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluene sulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include, but are not limited to, hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluene sulfonic acid, uric acid and the like.

Kits

In one aspect, the disclosure provides a kit for pain management, comprising a unit pharmaceutical composition comprising about 20 mg to about 120 mg of an opioid agonist (e.g., about 30 mg, about 60 mg, e.g., about 20 mg to about 80 mg); about 25 mg, about 50 mg, or about 100 mg hydroxyzine HCl; a pharmaceutically acceptable excipient; about 150 mg, about 300 mg, about 600 mg, or about 1200 mg gabapentin; about 2 mg, or about 4 mg ondansetron HCl; and optionally about 50 mg or about 100 mg docusate sodium. In some embodiments, the opioid agonist is codeine phosphate.

In certain embodiments, a kit of the present disclosure comprises 1, 2, 3, 4, 5, 6, 7, 8, 9, 10, 11, 12, 13, 14, 15, 16, 17, 18, 19, 20 or more units. In some embodiments, a kit of the present disclosure comprises one, two, three or more units.

In some embodiments, the kits may include a pharmaceutical composition as described herein, in suitable packaging, and written material that can include instructions for use, discussion of clinical studies, listing of side effects, and the like. Such kits may also include information, such as scientific literature references, package insert. materials, clinical trial results, and/or summaries of these and the like, which indicate or establish the activities and/or advantages of the pharmaceutical composition, and/or which describe dosing, administration, side effects, drug interactions, or other information useful to the health care provider.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" may be a single tablet or capsule or several tablets or capsules to be taken on a given day.

It should be noted, throughout the description, where compositions are described as having, including, or comprising specific components, it is contemplated that further embodiments include compositions that consist essentially of, or consist of, the recited components. Similarly, where processes are described as having, including, or comprising specific process steps, further embodiments are contemplated wherein the processes also consist essentially of, or consist of, the recited processing steps. Except where indicated otherwise, the order of steps or order for performing certain actions are immaterial so long as the disclosure remains operable. Moreover, unless otherwise noted, two or more steps or actions may be conducted.

EXAMPLES

Example 1

Evaluation for the Treatment of Chronic Pain

Method:

Administration of disclosed compositions to 20 patients was carried out as described below. The patients were required to score their pain while on their previous medications as shown. The score was the standardized one −10/10 methodology. The patients were then switched to a dose of Composition A as described below and were asked to report on their pain, using the same methodology.

Composition A: codeine sulfate (120 mg unless otherwise indicated, 100 mg hydroxyzine pamoate, 300 mg gabapentin).

TABLE 1

| | Morphine Milligram equivalents | | | | | | |
|---|---|---|---|---|---|---|---|
| | MME Conversion Factor | mg | MME/dose | MME/Day | CDC Daily Limit | Composition A: MME/dose | Composition A: MME/Day |
| Fentanyl Patch | 7.2 | 50 | 360 | 360 | 90 | 18 | 54 |
| Hydromorphon | 4 | 4 | 24 | 96 | 90 | 18 | 54 |
| Methadone | 8 | 40 | 320 | 960 | 90 | 18 | 54 |
| Hydrocodone | 1 | 75 | 75 | 225 | 90 | 18 | 54 |
| OxyContin | 1.5 | 80 | 120 | 360 | 90 | 18 | 54 |
| Oxymorphone | 3 | 60 | 180 | 540 | 90 | 18 | 54 |
| Oxycodone | 1.5 | 80 | 120 | 360 | 90 | 18 | 54 |
| Codeine | 0.15 | 120 | 18 | 54 | 90 | 18 | 54 |

Patient A
  a. Previous medication: Fentanyl Patch 50 μg, Oxycodone 15 mg PO Q6—Reported pain level—2/10
  b. Administered Composition A; Reported pain level—1/10
Patient B
  a. Previous medication: OxyContin 30 mg BID, Oxycodone 15 mg Q ID—Pain level—4/10
  b. Administered Composition A (with codeine 60 mg) PO Q8—Pain level—0-1/10
Patient C
  a. Previous medication: Fentanyl patch 75 μg, Klonopin 0.5 mg PO Bid, Oxycodone 15 PO QId, Fioricet for headaches—Pain level—3-4/10
  b. Administered Composition A—Pain level—3-4/10; Patient requested to continue Composition A. PSP—medication did not work for this patient
Patient D
  a. Previous medication: Fentanyl patch 75 μg, 15 mg Oxycodone QId—Pain level—2-3/10
  b. Administered Compound A (with codeine 60 mg)—PO TID—Pain level—2-3/10; patient mentioned increased mental clarity with Compound A
Patient E
  a. Previous medication: Fentanyl patch 75 μg, 15 mg Oxycodone QId, Klonopin 0.5 mg PO hs?, Neurontin 600 mg po q 8, Lyrica 75 mg PO Q8—Pain level—5-6/10
  b. Administered Compound A—Pain Level—4/10
Patient F
  a. Previous medication: Oxycodone 15 PO Q6, Flexural 10 PO TID, Morphine 30 mg PO Q 12—Pain level—6/10
  b. Administered Compound A+docusate sodium 100 mg+ondansetron HCl 4 mg—Pain Level—5/10
Patient G
  a. Previous medication Morphine 60 mg PO QA, Oxycodone 10 PO Q6—Pain level—6/10
  b. Compound A—Pain level—2-3/10
Patient H
  a. Previous medication: Methadone 10 QID, Oxycodone 15 mg Q ID—Pain level—4/10
  b. Composition A—Pain level—3/10 with some fatigue
Patient I
  a. Previous medication Oxycodone 15 PO QID—Pain—3/10 b. Composition A—Pain level—2-3/10; Patient had increased stomach pain and constipation, as well as dry mouth Patient J
a. Previous medication Oxycodone 15 mg PO QI, OxyContin 20 mg PO BID—Pain level—4/10
b. Composition A—Pain level—3/10

Patient K
a. Percocet, Gabapentin, Flexural—Pain level—3/10
b. Composition A—Pain level—2-3/10

Patient L
a. Previous medication Oxycodone 15 mg PO QID pain with Oxycodone/OxyContin—Pain level—2-3/10
b. Composition A—Pain level—2/10—patient indicated much more tolerable Patient M
a. Previous medication Lyrica 200 PO Q8, Methadone 10 mg one PO Q ID—Pain level—2/10
b. Administered Compound A; one tablet TID; Patient stayed with one Methadone daily—Pain level—2/10

Patient N
a. Previous medication: Oxycodone 15 PO Q ID, Morphine 30 ER 28, Klonopin 0.5 PO BID, Lyrica 75 mg PO Q8—Pain level—3-4/10
b. Composition A—Pain level—2-3/10; Patient felt residual stiffness but not pain Patient O
a. Previous medication: Oxycodone 20 PO Q6, OxyContin 40 mg ER one PO Q 12—Pain level—8-9/10
b. Composition A—Pain Level—5

Patient P
a. Previous medication: Fentanyl patch 100 μg, Oxycodone 15 mg PO Q I—Pain level—7/10
b. Composition A—Pain Level—4-5/10

Patient Q
a. Previous medication: Oxycodone 15 PO Q ID, Morphine 30 mg ER one PO Q 12—Pain Level—4-5/10
b. Composition A:—Pain level—3/10; patient experienced no withdrawal symptoms Patient R
a. Previous medication: Baclofen 20 mg PO Q8, Gabapentin 600 mg PO Q8, OxyContin PO Q12, Oxycodone 15 PO Q6—Pain level—3/10
b. Composition A (with codeine 60 mg)—Pain Level—4-5/10—Patient's pain increased, required an additional dose, indicating this patient should have started on Composition A (120 mg Codeine)

Patient S
a. Previous medication Morphine 60 mg ER TID, Oxycodone 15 mg PO QID—Pain level—6/10
b. Composition A—Pain level—2/10; Patient slept through the night. Patient stated that they felt the best they had in a long time Patient T
a. Previous medication: Oxycodone 15 mg PO Q6, Morphine 30 mg PO Q8, Flexural 10 PO TID, Klonopin 0.51QHS, Lyrica 150 PO TID, Flexural 10 PO QID—Pain level—4/10
b. Administered Composition A—Pain level—2-3/10; Patient reported lowest pain level years. Patient was able to sleep Patients were identified in a pain management practice. Each patient was on a moderate to high dose of narcotic analgesia. Patients were asked and agreed to participate in the study. All patients discontinued their previous pain medication 12 hours prior to starting the new medication. The patients were provided with either Composition A 60 mg or Composition A 120 mg+Composition B (docusate sodium 100 mg; ondansetron HCl 4 mg). The patients were selected for Composition A codeine amount depending on total dosage of narcotics. The patients were provided with Composition A 60 mg if their MME was less than 180. The patients were provided with Composition A 120 mg if their MME was 180 or greater.

The patients were seen individually and interviewed as to last dose of medication and present pain level. They were asked about withdrawal symptoms and potential side-effects. Vital signs were recorded. Patients were given Composition B and Composition A. The patients were monitored for 30 minutes to watch for allergic reactions or serious adverse reactions. Patients were then discharged with instructions to call the office if any reaction occurs; and return in the morning to be re-evaluated.

The patients were evaluated the next morning. They were instructed to stay on their Composition A prescription schedule and take the break-through medication as usual. The only medication change was to Composition A for their long acting medication.

The patients were asked to rate their pain score while taking composition A. The questions were the same as when their pain was evaluated while taking their previous pain medication. The patient gave a score of 1-10. This score was recorded along with any adverse reactions or special notations.

Results:
A total of 20 patients were evaluated. The patient's treatment medications ranged from a Duragesic patch 100 μg Q 72, Morphine 100 mg PO Q8 to OxyContin 80 mg PO Q8. This was compared to a proprietary blended combination of Codeine Sulfate 120 mg, Vistaril 100 mg with Zofran 4 mg, Gabapentin 300 mg and Colace 100 mg; TID.

Two scores were compared using a student t-test. The student's t-test revealed a probability of the assuming null hypothesis was 0.006. This indicated that the two pain scores were significantly different from one another and constituted different populations. The total for the treatment medications rebuild a pain score of 88. The total of the scores for the blended treatment was 58.

The results were evaluated using the Student T calculation. The null hypothesis is that Composition A reduces pain better than standard treatment.

Student's t-Test: Results
The results of an unpaired t-test performed at 21:49 on 29 May 2018
$t=2.93$
$sdev=1.51$
degrees of freedom=38
The probability of this result, assuming the null hypothesis, is 0.006
Group A: Number of Items=20
2.00 2.00 3.00 3.00 3.00 3.00 3.00 4.00 4.00 4.00 4.00 4.00 4.00 5.00 6.00 6.00 6.00 6.00
7.00
9.00
Mean=4.40
95% confidence interval for Mean: 3.716 through 5.084
Standard Deviation=1.79
Hi=9.00 Low=2.00
Median=4.00
Average Absolute Deviation from Median=1.30
Group B: Number of Items=20
1.00 1.00 2.00 2.00 2.00 2.00 3.00 3.00 3.00 3.00 3.00 3.00 3.00 3.00 4.00 4.00 5.00
5.00

5.00
Mean=3.00
95% confidence interval for Mean: 2.316 through 3.684
Standard Deviation=1.17
Hi=5.00 Low=1.00
Median=3.00
Average Absolute Deviation from Median=0.800

The Student T test confirms that this finding is an independent finding and the statistical significance is P<0.0006.

INCORPORATION BY REFERENCE

The entire disclosure of each of the patent documents and scientific articles referred to herein is incorporated by reference for all purposes.

Equivalents

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

What is claimed:

1. A pharmaceutical composition comprising:
   codeine or a pharmaceutically acceptable salt thereof;
   hydroxyzine or a pharmaceutically acceptable salt thereof;
   a gabapentinoid;
   optionally a 5-HT3 antagonist; and
   a pharmaceutically acceptable excipient.

2. The pharmaceutical composition of claim 1, wherein the 5-HT3 antagonist is present and is selected from the group consisting of ondansetron or a pharmaceutically acceptable salt thereof, tropisetron, granisetron, dolasetron, palonosetron, ramosetron, galanolactone, mirtazapine, olanzapine, cisapride, renzapride and metoclopramide.

3. The pharmaceutical composition of claim 2, wherein the 5-HT3 antagonist is ondansetron or a pharmaceutically acceptable salt thereof.

4. The pharmaceutical composition of claim 1, wherein the gabapentinoid is selected from the group consisting of gabapentin or a pharmaceutically acceptable salt thereof, gabapentin encarbil, and atagabalin.

5. The pharmaceutical composition of claim 1, comprising gabapentin and ondansetron HCl.

6. The pharmaceutical composition of claim 1, further comprising a stool softener and/or a constipation agent, wherein the stool softener or constipation agent is docusate or a pharmaceutically acceptable salt thereof, or naloxegol.

7. The pharmaceutical composition of claim 1, wherein the pharmaceutically acceptable excipient is methyl cellulose.

8. The pharmaceutical composition of claim 1, wherein the composition comprises about 20 mg to about 120 mg codeine or a pharmaceutically acceptable salt thereof.

9. The pharmaceutical composition of claim 1, wherein the composition comprises about 60 mg or about 120 mg codeine phosphate.

10. The pharmaceutical composition of claim 8, wherein the composition comprises about 50 mg or about 100 mg docusate sodium.

11. The pharmaceutical composition of claim 1, wherein the composition comprises about 10 mg to about 110 mg hydroxyzine or a pharmaceutically acceptable salt thereof.

12. The pharmaceutical composition of claim 7, wherein the composition comprises about 1 mg to about 4 mg ondansetron HCl.

13. The pharmaceutical composition of claim 7, wherein the composition comprises about 100 mg to about 1200 mg gabapentin.

14. A pharmaceutical composition for treating neuropathic and deep tissue pain, comprising:
    (a) about 60 mg or about 120 mg codeine phosphate;
    (b) about 50 mg or about 100 mg hydroxyzine HCl;
    (c) about 4 mg ondansetron HCl;
    (d) about 300 mg or about 1200 mg gabapentin;
    (e) about 100 mg docusate sodium; and
    (f) a pharmaceutically acceptable excipient for controlled release.

15. A pharmaceutical composition comprising:
    about 60 mg or 120 mg codeine phosphate;
    about 20 mg to about 100 mg hydroxyzine HCl;
    optionally about 150 mg to about 600 mg gabapentin; and
    a pharmaceutically acceptable excipient.

16. The pharmaceutical composition of claim 15, further comprising about 1 mg to about 4 mg ondansetron HCl.

17. An unit pharmaceutical composition comprising:
    about 30 mg or about 60 mg codeine phosphate;
    about 25 mg or about 50 mg hydroxyzine HCl;
    about 150 mg, about 300 mg, about 600 mg, or about 1200 mg gabapentin;
    about 2 mg ondansetron HCl;
    about 50 mg docusate Na; and
    a pharmaceutically acceptable excipient.

18. The pharmaceutical composition of claim 1, wherein when administered to a patient one, two or three times daily, provides a substantially lower pain score as compared to a patient's pain score when administered a fentanyl patch 50 µg or 70 µg; oxycodone 15 mg orally every 6 hours, 2 times daily or 4 times daily, oxycodone 30 mg twice daily, morphine 30 mg every 12 hours, or any combination thereof.

19. The pharmaceutical composition of claim 1, wherein when administered to a patient one, two or three times daily, provides a substantially less dysphoria or withdrawal symptoms as compared to a patient's pain score when administered a fentanyl patch 50 µg or 70 µg; oxycodone 15 mg orally every 6 hours, 2 times daily or 4 times daily, oxycodone 30 mg twice daily, morphine 30 mg every 12 hours, or any combination thereof.

20. The pharmaceutical composition of claim 1, wherein when administered to a patient one, two or three times daily, the patient has improved mental clarity as compared to a patient when administered a fentanyl patch 50 µg or 70 µg;
    oxycodone 15 mg orally every 6 hours, 2 times daily or 4 times daily, oxycodone 30 mg twice daily, morphine 30 mg every 12 hours, or any combination thereof.

21. The pharmaceutical composition of claim 1, wherein the composition provides about 20 MME or less of the codeine per dose, or less than 90 MME per day, when administered one, two or three times a day.

22. A method of treating neuropathic and nociceptive pain in a patient in need thereof comprising administering to the patient a composition of claim 1.

* * * * *